US 9,541,515 B2

(12) United States Patent
Hoefnagels et al.

(10) Patent No.: US 9,541,515 B2
(45) Date of Patent: Jan. 10, 2017

(54) CHARACTERIZATION APPARATUS

(71) Applicant: Xeikon IP B.V., Eede (NL)

(72) Inventors: Kim Louis Jozephus Hoefnagels, Schoten (BE); Herman Jan Godelieve Van De Straete, Deurne (BE); Herwig Joannes Van Dooren, Weerde (BE); Bjorn Leynen, Deurne (BE)

(73) Assignee: Xeikon IP B.V., Eede (NL)

( * ) Notice: Subject to any disclaimer, the term of this patent is extended or adjusted under 35 U.S.C. 154(b) by 8 days.

(21) Appl. No.: 14/797,293

(22) Filed: Jul. 13, 2015

(65) Prior Publication Data
US 2016/0011137 A1    Jan. 14, 2016

(30) Foreign Application Priority Data

Jul. 14, 2014   (EP) ..................................... 14176960
Nov. 27, 2014   (EP) ..................................... 14195096

(51) Int. Cl.
| | |
|---|---|
| *G01R 27/26* | (2006.01) |
| *G03G 15/10* | (2006.01) |
| *G01N 27/22* | (2006.01) |
| *G01N 27/07* | (2006.01) |
| *G01D 5/24* | (2006.01) |
| G06F 3/044 | (2006.01) |

(52) U.S. Cl.
CPC .......... *G01N 27/226* (2013.01); *G01D 5/2405* (2013.01); *G01N 27/07* (2013.01); *G01R 27/26* (2013.01); *G01R 27/2605* (2013.01); *G03G 15/105* (2013.01); *G06F 3/044* (2013.01)

(58) Field of Classification Search
CPC ... G01D 5/2405; G01R 27/26; G01R 27/2605; G06F 3/044; G03G 15/105; G03G 15/065; G03G 15/50

USPC ......... 324/76.77–76.83, 459, 600, 649, 658, 324/663; 399/9, 38, 53, 57, 75, 92, 107, 399/128, 130, 187, 343
See application file for complete search history.

(56) References Cited

U.S. PATENT DOCUMENTS

| | | |
|---|---|---|
| 5,598,251 A | 1/1997 | Parish et al. |
| 6,613,209 B2 | 9/2003 | Ozerov |
| 9,035,661 B2 * | 5/2015 | Andersson ............. G01N 27/07 324/438 |

(Continued)

FOREIGN PATENT DOCUMENTS

GB    2300924 A    11/1996

*Primary Examiner* — Jermele M Hollington
*Assistant Examiner* — Raul Rios Russo
(74) *Attorney, Agent, or Firm* — The Webb Law Firm (57) ABSTRACT

A characterization apparatus for characterizing a liquid containing insoluble particles includes a housing including an inlet portion defining an inlet passage between an inlet end and a first channel end, a channel portion defining a measurement channel between the first channel end and a second channel end, and an outlet portion defining an outlet passage between the second channel end and an outlet end. The channel portion includes a first electrode and a second electrode at a first and second side of the channel. The apparatus also includes a measurement device configured for measuring an electric measure representative for properties of the liquid flowing between the first electrode and the second electrode. The inlet passage gradually changes shape from the inlet end to the first channel end. The outlet passage gradually changes shape from the second channel end to the outlet end.

20 Claims, 7 Drawing Sheets

(56) References Cited

U.S. PATENT DOCUMENTS

2010/0006441 A1* 1/2010 Renaud ............ B01L 3/502746
 204/643
2014/0091012 A1* 4/2014 Ros ........................ B03C 5/005
 209/129

* cited by examiner

CHARACTERIZATION APPARATUS

CROSS-REFERENCE TO RELATED APPLICATIONS

This application claims priority to European Patent Application Nos. 14 176 960.4 and 14 195 096.4, filed Jul. 14, 2014 and Nov. 27, 2014, respectively, the disclosures of which are hereby incorporated in their entirety by reference.

FIELD OF INVENTION

This invention relates to a characterization apparatus for characterizing a liquid containing insoluble particles, and in particular for determining a solid content and/or conductivity of the liquid. Particular embodiments relate to the field of toner characterization apparatus capable of measuring an electric measure representative for an electric current through liquid toner flowing between two electrodes. Also, the invention relates to a printing apparatus comprising such a toner characterization apparatus, and to a toner preparing apparatus comprising such a toner characterization apparatus.

BACKGROUND

U.S. Pat. No. 6,613,209 discloses a toner characterization cell adapted to determine characteristics of insoluble particles in a liquid medium by measuring an electric displacement current between a first and a second electrode and by measuring optical densities at the first and second electrodes.

Many liquids containing insoluble particles, such as liquid toners, show non-Newtonian behavior. Typically, the viscosity of non-Newtonian fluids is dependent on shear rate or shear rate history. This non-Newtonian behavior often leads to sedimentation problems when the liquid has to flow through a channel.

SUMMARY

Embodiments of the invention aim to provide a characterization apparatus for characterizing liquid containing insoluble particles in a convenient manner, avoiding or significantly reducing sedimentation problems and allowing obtaining accurate measurement results.

According to a first aspect of the invention there is provided a characterization apparatus comprising a housing with an inlet portion defining an inlet passage between an inlet end and a first channel end, a channel portion defining a measurement channel between the first channel end and a second channel end, and an outlet portion defining an outlet passage between the second channel end and an outlet end, such that the liquid can be circulated from the inlet passage, through the measurement channel, to the outlet passage. The channel portion comprises a first electrode and a second electrode at a first and second side of the channel. The characterization apparatus further comprises a measurement device configured for measuring an electric measure which is representative for the properties of the liquid between the first electrode and the second electrode. The measurement channel has a length in a flow direction between said first channel end and said second channel end, and a thickness seen in a direction perpendicular to the flow direction corresponding with a distance between said first and said second electrode. The length is at least 5 times larger than said thickness. The inlet passage gradually changes shape from the inlet end to the first channel end; and the outlet passage gradually changes shape from the second channel end to the outlet end.

Embodiments of the invention are based inter alia on the insight that by providing a suitable liquid flow between the first and second electrode, accurate measurements may be obtained whilst avoiding sedimentation. This is reached by providing on the one hand a measurement channel having suitable dimensions, resulting in a relatively long stable flow between the electrodes, such that the measurements are not significantly influenced by boundary effects, and, by providing on the other hand, suitable inlet and outlet portions which "guide" the liquid flow to the measurement channel, avoiding or significantly reducing sedimentation.

In a preferred embodiment the length is at least 10 times larger than the thickness, more preferably at least 20 times, even more preferably at least 30 times, and most preferably at least 50 times larger than the thickness. In that way the accuracy of the measurements can be further improved.

In a preferred embodiment the first electrode contacts the channel, in a section perpendicular to the flow direction, over a first distance, and the second electrode contacts the channel, in a section perpendicular to the flow direction, over a second distance. Preferably, the first and second distances are at least 5 times larger than the thickness. More preferably, the first and second distances are at least 10 times larger than the thickness, even more preferably at least 20 times, even more preferably at least 30 times, and most preferably at least 50 times larger than the thickness.

In a preferred embodiment the measurement device is a current measurement device configured for measuring an electric measure representative for an electric current through the liquid flowing between the first and the second electrode, upon application of a variable voltage between the first and the second electrode. Such measurements will allow determining the solid content and/or the conductivity of the liquid flowing between the electrodes.

According to a preferred embodiment the inlet passage gradually changes shape from the shape of a tube passage at said inlet end to the shape of the measurement channel at said first channel end. In a similar manner, preferably, the outlet passage gradually changes from the shape of the measurement channel at said second channel end to the shape of a tube passage at said outlet end.

According to a preferred embodiment the inlet passage, the measurement channel, and the outlet passage are shaped for creating a flow of the liquid in the measurement channel in the flow direction, such that said flow, seen in a section perpendicular to said flow direction, has an average velocity va, and the velocity v in at least 90% of the section fulfills va−0.1*va<v<va+0.1*va. In other words, the flow in the measurement channel, as seen in a section perpendicular to said flow direction is preferably more or less spatially uniform, allowing to perform accurate measurements. In a further developed embodiment, the inlet and outlet portions are shaped such that also in the inlet and outlet portions, in a section (in certain embodiments this will be a non-flat section) perpendicular to the flow direction, the velocity v in at least 90% of the section fulfills va−0.1*va<v<va+0.1*va, wherein va is the average velocity of the section.

According to a preferred embodiment the measurement channel has a constant cross section, perpendicular on the flow direction corresponding with the flow direction of the liquid in the measurement channel.

According to a further developed embodiment the first electrode is a hollow inner cylinder and the second electrode is a hollow outer cylinder placed around the inner cylinder, wherein said outer and inner cylinders define the measurement channel Preferably, the outer cylinder and inner cylinder have a common axis. Preferably the measurement device is located inside the inner cylinder. In that way the inner cylinder protects the measurement device against electromagnetic interference.

According to another exemplary embodiment the first and second electrode are plates spaced at a constant distance from each other.

According to a preferred embodiment the inlet portion is shaped with a tube passage at said inlet end, said tube passage connecting to a ring passage, and said ring passage connecting to the first channel end of the measurement channel The tube passage and the ring passage together form the inlet passage. In a possible embodiment, the tube passage has an axis which is offset with respect to the flow direction of the channel or which is oriented under an angle with respect to the flow direction of the channel, and the ring passage gradually narrows as the distance from the tube passage increases.

In a preferred embodiment the characterization apparatus comprises a voltage source configured for applying a variable voltage, e.g. a periodic alternating voltage such as a triangular wave voltage, a square wave voltage, or a sinusoidal wave voltage, between the first and the second electrode. The measurement device may comprise a current measurement module configured for measuring an electric measure representative the current flowing through the liquid between the first electrode and the second electrode for different values of the applied voltage. The current measurement module may comprise an amplifier configured for amplifying the electric current between the first and the second electrode. Further, the measurement device may comprise registration means for registering a measure representative for the (optionally amplified) current, and sending means for sending values derived from or based on the registered measure to an external device. According to an additional aspect of the invention, there is provided a characterization system comprising such a characterization apparatus and a computing device configured for receiving the values derived from or based on the registered measure, and for computing a value for the conductivity and solid content of the liquid containing insoluble particles, based on said received values.

According to a possible embodiment the characterization apparatus further comprises first and second optical density measurement devices arranged to measure a change in optical density adjacent the first and the second electrode. The presence of on the one hand a current measurement device and on the other hand first and second optical density measurement devices will allow to determine parameters of the liquid, such a solid content and conductivity, using another method. See also U.S. Pat. No. 6,613,209 mentioned in the background section.

According to a possible embodiment the first and/or second electrode may be provided with a coating. By providing a suitable coating chemical resistance problems due to a reaction of the toner liquid (in particular the dispersion agent thereof) with the copper electrodes, may be avoided. Alternatively or in addition, the coating may be chosen to reduce the surface energy and to reduce the surface roughness, so that the risks on having sedimentation on the electrodes are reduced. The coating may be a metallic coating, a non-metallic coating, or a composite coating including metallic and non-metallic materials. Indeed, because in embodiments of the invention the measurements may be high frequency AC measurements, an electrically conductive coating is not required.

Examples of suitable metallic coatings include: galvanizing (zinc-coating), nickel plating, chromatising, anodizing, gold plating, silver plating, phosphatising (e.g. zinc or manganese phosphatising). Such coatings may increase the hardness and/or decrease the surface roughness compared to an uncoated surface.

Examples of suitable non-metallic coatings include: a polytetrafluoroethylene (PTFE)-based coating (also known as Teflon-ising), varnishing, lacquering, ceramic coating. Such coatings may decrease the surface roughness and/or decrease the surface energy compared to an uncoated surface.

Examples of suitable combined metallic and non-metallic coatings include: a nickel-PTFE composite coating, such as a niflon coating. Such coatings may increase the hardness, decrease the surface roughness and decrease the surface energy compared to an uncoated surface.

According to another aspect of the invention, there is provided a digital printing apparatus using liquid toner comprising a reservoir storing liquid toner and a characterization apparatus according to any one of the above disclosed embodiments, said inlet end of said characterization apparatus being in fluid communication with an outlet of the reservoir.

In a preferred embodiment, the digital printing apparatus further comprises a toner component addition means, e.g. a carrier liquid addition means and/or a dispersion agent addition means and/or a concentrate addition means, for adding a toner component of said liquid toner, e.g. carrier liquid and/or dispersion agent and/or toner concentrate, and a controller configured for controlling said toner component addition means in function of the measurements performed by the measurement device of the characterization apparatus.

According to another aspect of the invention, there is provided a toner preparation apparatus for preparing liquid toner, comprising a characterization apparatus according to any one of the above disclosed embodiments. The toner preparation apparatus may comprise a milling means and a controller for controlling the milling means in function of the measurements performed by the measurement device of the characterization apparatus. More in particular, the controller may be configured to stop the milling process when the conductivity of the liquid toner, which is computed based on the performed measurements, is within a certain range. The toner preparation apparatus may further comprise a dispersion agent adding means, and the controller may be configured to control the dispersion agent adding means in function of the measurements performed by the measurement device. In further developed embodiments the controller may be configured to control a rotation speed of the milling means and/or a cooling module of the milling means in function of the measurements performed by the measurement device.

BRIEF DESCRIPTION OF THE FIGURES

The accompanying drawings are used to illustrate presently preferred non-limiting exemplary embodiments of devices of the present invention. The above and other advantages of the features and objects of the invention will become more apparent and the invention will be better understood from the following detailed description when read in conjunction with the accompanying drawings, in which.

DESCRIPTION OF EMBODIMENTS

FIGS. 1A-1D, 2 and 3 illustrate a first embodiment of a characterization unit for characterizing a liquid containing insoluble particles, typically a liquid toner. The characterization unit comprises a housing 10 with an inlet portion 20, a channel portion 30 and an outlet portion 40. The characterization unit further comprises measurement means 50 configured for measuring an electric measure representative for an electric displacement current in the liquid that is flowing through the channel portion.

The inlet portion 20 is provided with an inlet passage between an inlet end 21 and a first channel end 31. The channel portion 30 is provided with a measurement channel between the first channel end 31 and a second channel end 32. The outlet portion 40 is provided with an outlet passage between the second channel end 32 and an outlet end 41. The liquid can be circulated, e.g. through the use of a pump (not illustrated) from the inlet passage, through the measurement channel, to the outlet passage. The channel portion 30 comprises a first electrode 33 and a second electrode 34 at a first and second side of the measurement channel, respectively. The measurement device 50 is configured for measuring an electric measure representative for an electric current between the first electrode 33 and the second electrode 34, said current being the result of an electrical potential fluctuation applied between the electrodes 33, 34.

In the measurement channel the flow is preferably as uniform as possible in order to be able to obtain accurate measurement results. Preferably the flow is such that sedimentation is avoided or limited to a minimum. The measurement channel has a length (l) in a flow direction, here the axial direction A1, between the first channel end 31 and the second channel end 32, and a thickness (t) seen in a direction perpendicular to the flow direction corresponding with a distance between the first electrode 33 and the second electrode 34. To ensure a uniform flow the length (l) is preferably at least 5 times larger than the thickness (t), more preferably at least 10 times larger than the thickness (t), and most preferably at least 20 times larger than the thickness (t), and e.g. at least 50 times larger than the thickness (t). In an exemplary embodiment, the length (l) is between 60 mm and 300 mm, and the thickness (t) is between 1 mm and 3 mm.

In the first exemplary embodiment, the first electrode 33 is a hollow inner cylinder and the second electrode 34 is a hollow outer cylinder positioned around said inner cylinder. The outer cylinder 34 is concentric with the inner cylinder 33, and they have a common axis A1. The measurement channel is defined between the outer cylinder 34 and the inner cylinder 33, and has a constant thickness t which is equal to the difference between the inner radius of the outer cylinder R2 and the outer radius of the inner cylinder R1. In the example, the measurement device 50 is located inside the inner cylinder 33, but the skilled person understands that the measurement device 50 could also be located outside the outer cylinder 34. The cylindrical electrodes 33, 34 may be made of a suitable metal material, e.g. a copper alloy such as brass, or copper. The first and/or second electrodes 33, 34 may be provided with a coating. The coating may be chosen to reduce the surface energy and/or to reduce the surface roughness, so that the risks on having sedimentation on the electrodes are reduced. The coating may be a metallic coating, a non-metallic coating, or a composite coating including metallic and non-metallic materials. For examples of suitable coatings reference is made to the embodiments disclosed above.

The first cylindrical electrode 33 contacts the channel, seen in a section perpendicular to the axial direction A1, over a first distance which is equal to the circumference $2\pi*R1$, and the second cylindrical electrode 34 contacts the channel, seen in a section perpendicular to the axial direction A1, over a second distance which is equal to the circumference $2\pi*R2$. Preferably, the first and second distance ($2\pi*R1$, $2\pi*R2$) are at least 5 times larger than the thickness (t), more preferably at least 10 times larger than the thickness (t), and most preferably at least 20 times larger than the thickness (t).

The inlet passage gradually changes shape from the inlet end 21 to the first channel end 31, and, more in particular, changes shape from the shape of a tube passage 22 at said inlet end 21 to the shape of the measurement channel at said first channel end 31. The inlet portion 20 comprises a first part 20a and a second part 20b. The first part 20a is shaped as a tube passage 22 at said inlet end 21, and the tube passage 22 is connected to a ring shaped passage 23 which is partly delimited by the first part 20a and partly by the second part 20b. The ring shaped passage 23 is connected to the first channel end 31 of the measurement channel. The tube passage 22 and said ring passage 23 together form the inlet passage. In the illustrated embodiment the tube passage 22 has an axis A2 which is perpendicular to the axis A1 of the measurement channel. However in an alternative embodiment the axis A2 could also be oriented under a different angle with respect to the axis A1. The ring passage 23 gradually narrows as the distance from the tube passage 22 increases, so as to compensate for the amount of liquid flowing upward in the measurement channel. In the illustrated embodiment, the bottom of ring shaped passage raises gradually from right to left, i.e. as the distance from the tube passage 22 increases.

In the illustrated embodiment, the outlet portion 40 is identical to the inlet portion 20, but is mounted upside down. The outlet portion 40 comprises a first part 40a and a second part 40b. The outlet passage gradually changes shape from the shape of the measurement channel at the second channel end 32 to the shape of a tube passage at the outlet end 41.

Part 20a of the inlet portion 20 is further provided with an annular recess 25 for receiving a first end of the outer cylinder 34, wherein O-rings 26 ensure a liquid-tight assembly. In a similar way, part 40a of the outlet portion 40 is provided with an annular recess 45 for receiving a second end of the outer cylinder 34, wherein O-rings 46 ensure a liquid-tight assembly. Also parts 20a and 40a are provided with a central through opening 27, 47 for receiving first ends of parts 20b, 40b, in a liquid-tight manner using O-rings 28, 48, respectively. The parts 20b, 40b have second ends which are configured for receiving a first and second end of the inner cylinder 33, respectively. The parts 20b, 40b are further provided with a through opening 29, 49, respectively, extending in the direction of axis A1, for allowing cables to enter in/out of the inner cylinder 33.

Figure 1A:
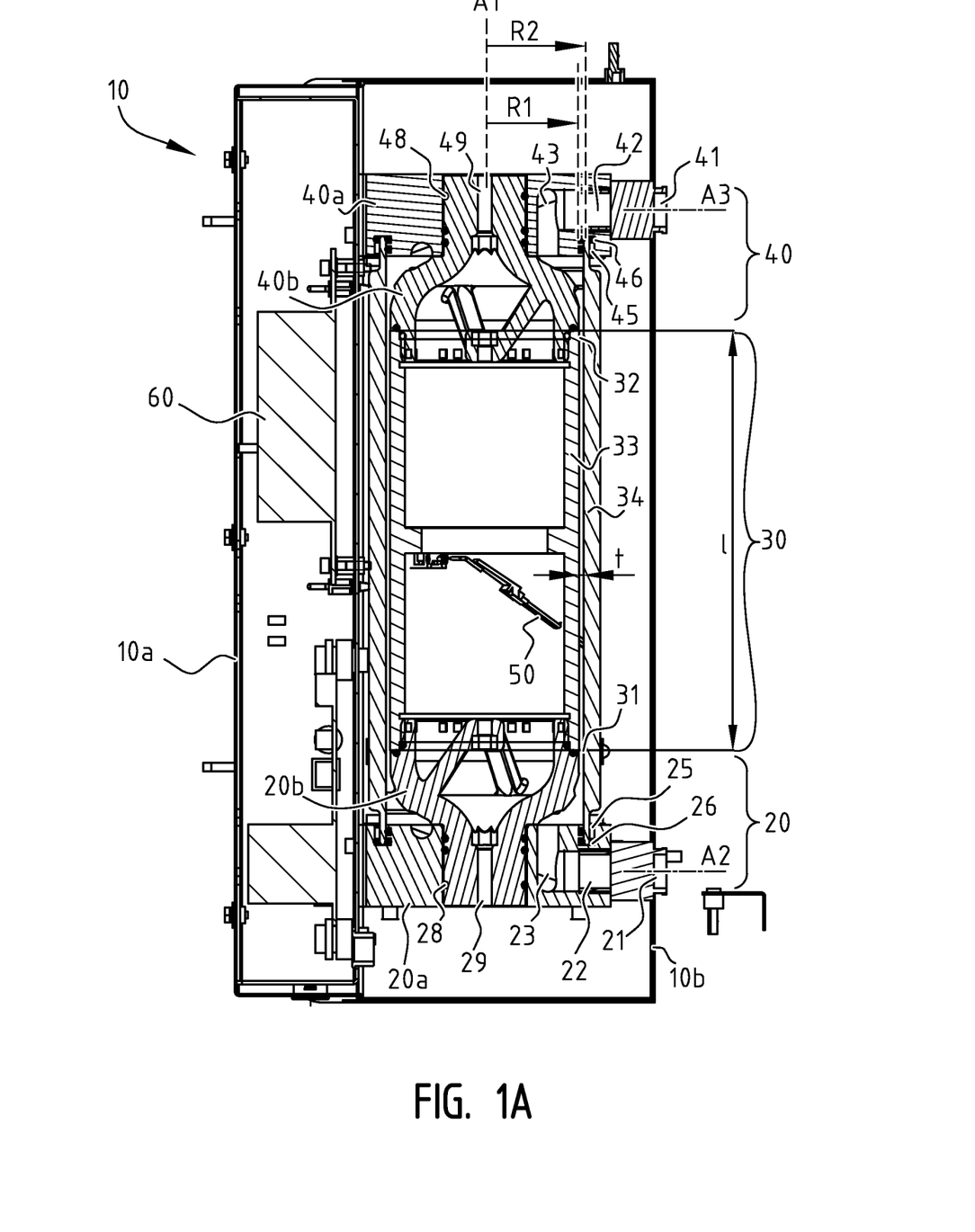
FIG. 1A is a sectional view of a first embodiment of a characterization apparatus, in particular suitable for characterizing a liquid toner.
Figure 1B:
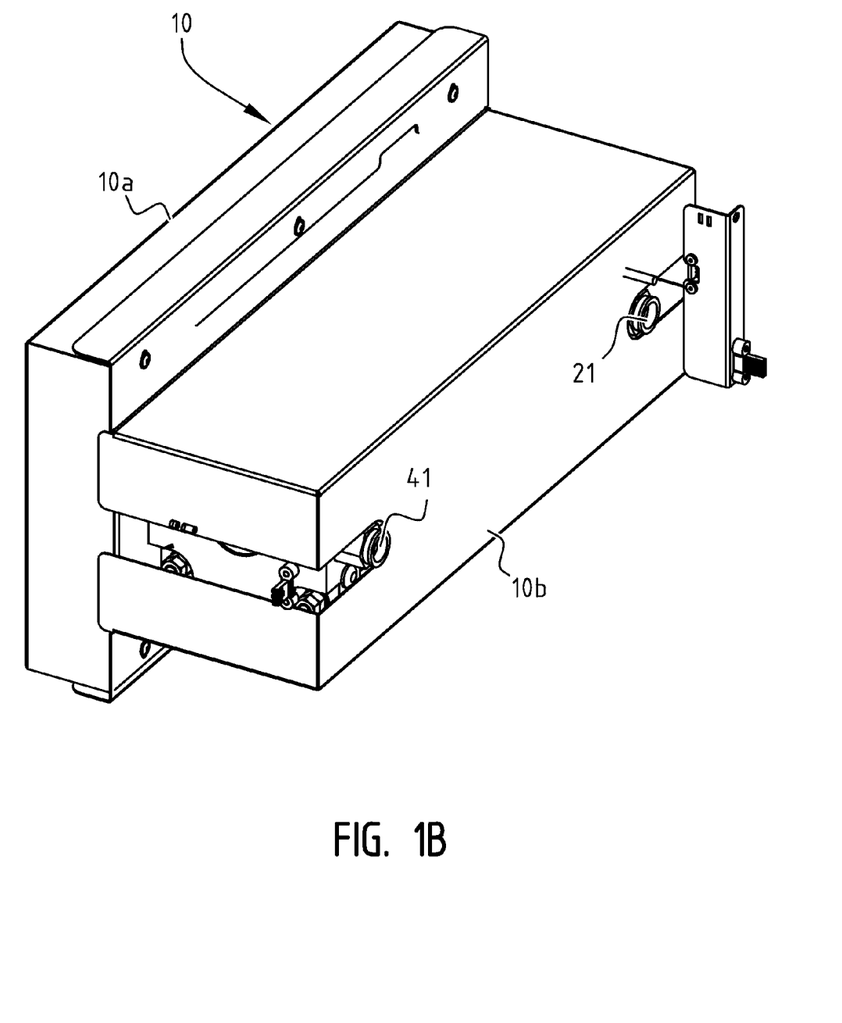
FIG. 1B is a perspective view of the characterization apparatus of FIG. 1A.
Figure 1C:
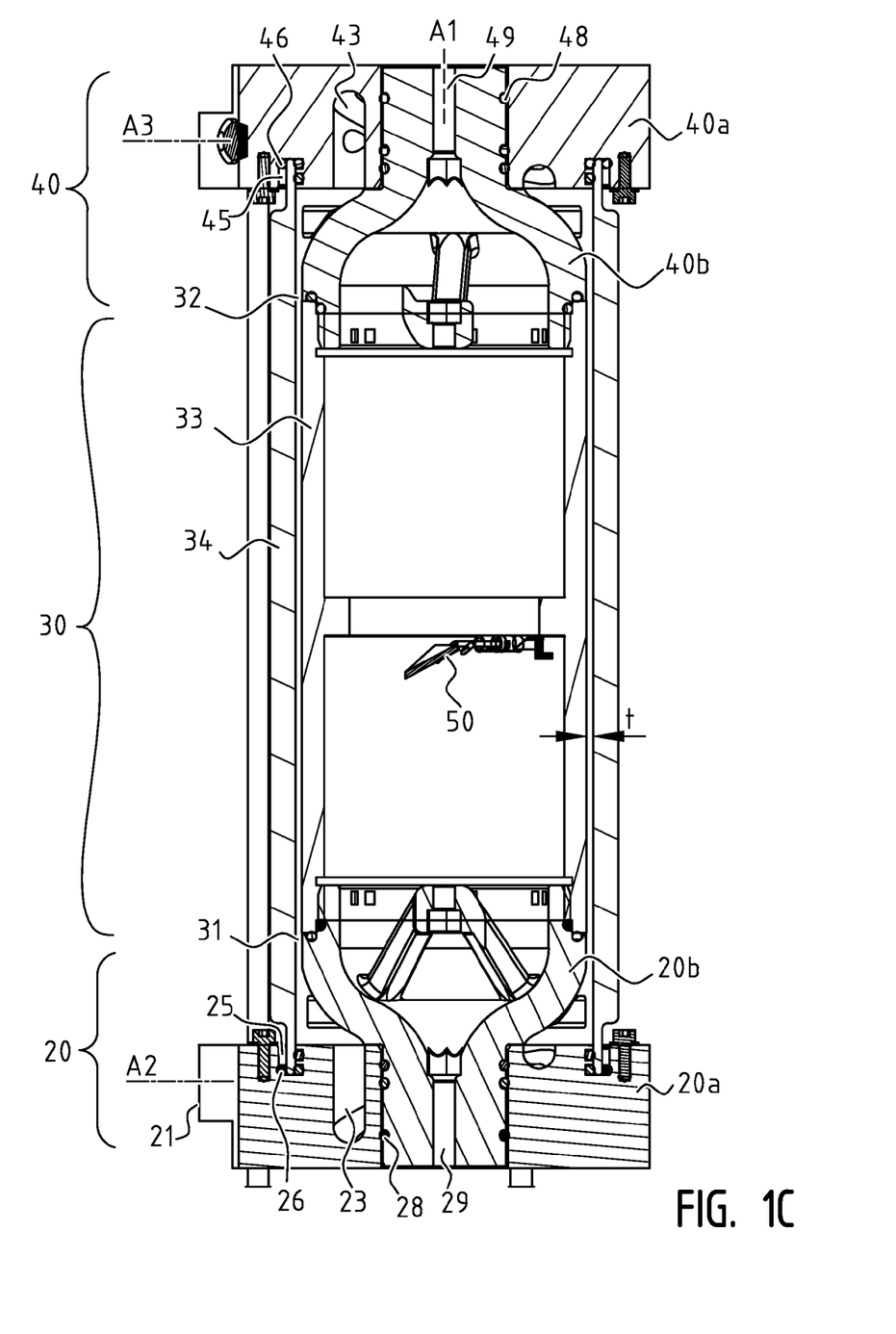
FIG. 1C is a sectional view of the characterization apparatus of FIG. 1A without the housing.

The housing 10 comprises a first part 10a creating a first cage of Faraday and a second part 10b creating a second cage of Faraday. In that way, noise can be reduced, and the measurement accuracy of the measurements performed by measurement device 50 may be improved.

The inlet passage, the measurement channel, and the outlet passage are shaped for creating a flow of the liquid in said measurement channel in the flow direction, such that said flow, seen in a section perpendicular to said flow direction A1, has an average velocity va. Preferably, the velocity v in 90 percent of the section fulfills $va-0.1*va<v<va+0.1*va$, i.e. the velocity does not vary more than 10% above or below the average velocity.

Figures 1D, 2:
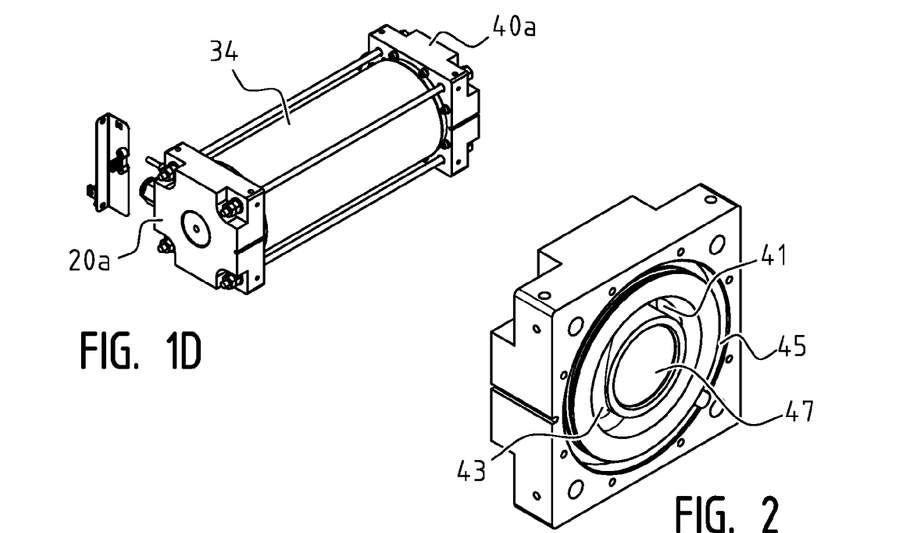
FIG. 1D is a perspective view of the characterization apparatus of FIG. 1A without the housing.
FIG. 2 is a perspective view of a part of the inlet portion (or outlet portion) of the characterization apparatus of FIG. 1A.
Figure 3:
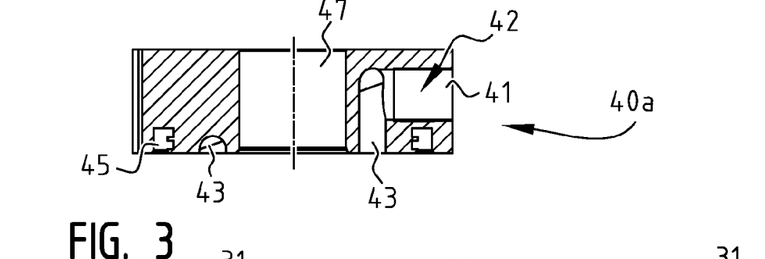
FIG. 3 is a section view of the part of the inlet portion (or outlet portion) of FIG. 2.
Figure 4:
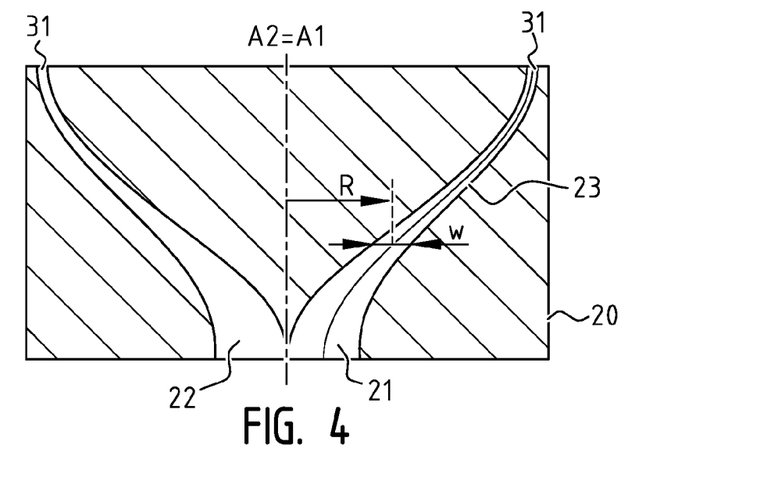
FIG. 4 is sectional view of a variant of the inlet portion (or outlet portion) of the characterization apparatus of FIG. 1A.

FIG. 4 illustrates a schematic cross section of a variant of the inlet portion 20 of FIGS. 1-3. In this embodiment, the inlet passage is shaped also as a tube passage 22 at the inlet end 21, but the tube passage has an axis A2 which corresponds with the axis A1 of the measurement channel. The tube passage 22 is connected to a ring shaped passage 23 which gradually narrows in the direction of the measurement channel. Because the tube passage is aligned with the axis A1, the ring shaped passage has a constant width w seen in a cross section perpendicular to the axis A1. In a preferred embodiment the width w gradually decreases from the tube passage 22 to the first channel end 31, whilst the average radius R of the ring shaped channel gradually increases, such that w*R is more or less constant over a trajectory.

Figure 5:
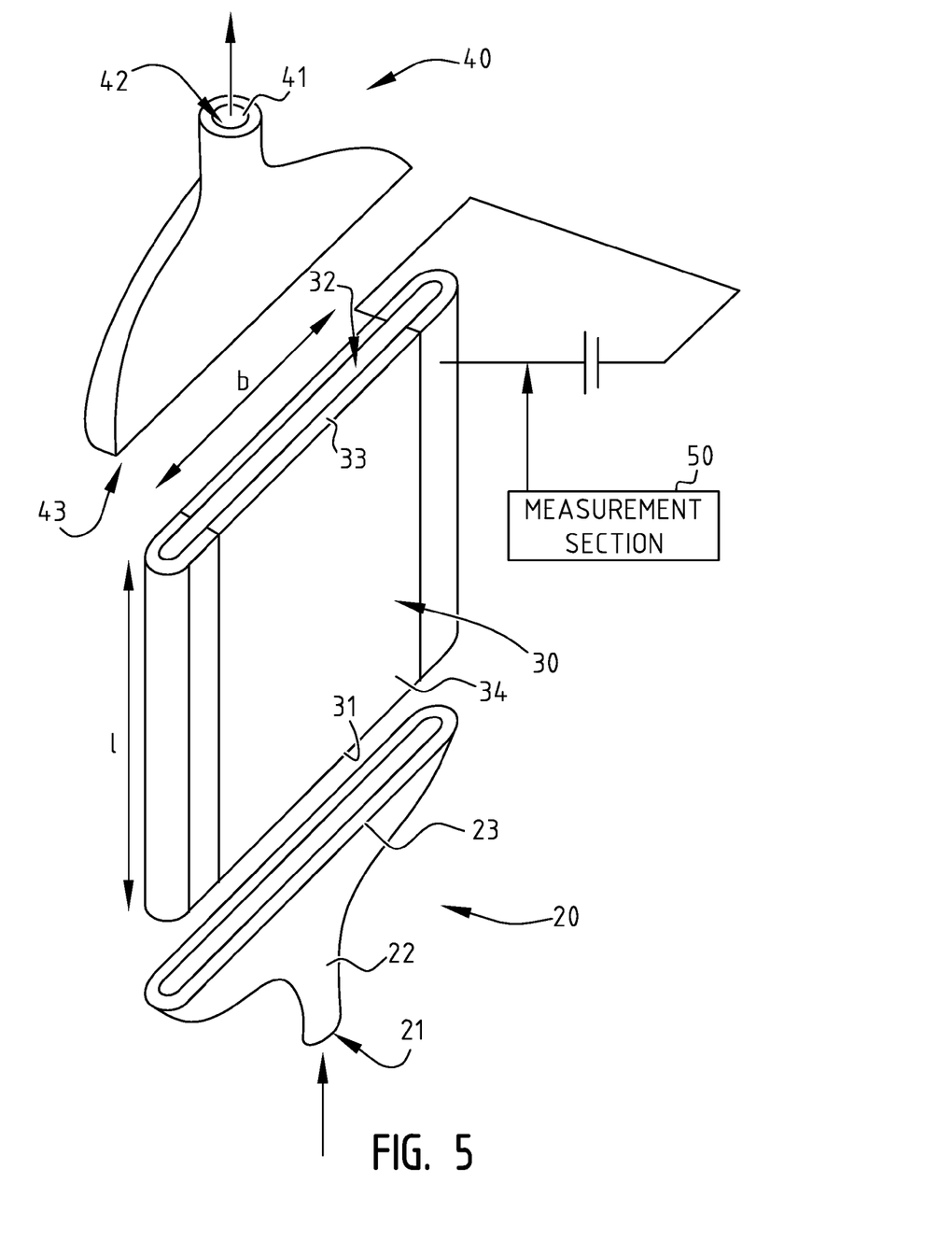
FIG. 5 is a perspective view of a second embodiment of a characterization apparatus.

FIG. 5 illustrates a second embodiment of a characterization unit for characterizing a liquid containing insoluble particles, typically a liquid toner. The characterization unit comprises a housing (not shown) with an inlet portion 20, a channel portion 30 and an outlet portion 40, and with a measurement device 50 configured for measuring an electric measure which is representative for the properties of the liquid that is flowing through the channel portion. The inlet portion 20 is provided with an inlet passage between an inlet end 21 and a first channel end 31. The channel portion 30 is provided with a measurement channel between the first channel end 31 and a second channel end 32. The outlet portion 40 is provided with an outlet passage between the second channel end 32 and an outlet end 41.

The channel portion 30 comprises a first plate electrode 33 and a second plate electrode 34 at a first and second side of the measurement channel, respectively. The measurement section 50 is configured for measuring an electric measure (typically a voltage or a current) representative for an electric current between the first electrode 33 and the second electrode 34. The measurement channel has a length (l) in a flow direction, between the first channel end 31 and the second channel end 32, and a thickness (t) seen in a direction perpendicular to the flow direction corresponding with a distance between the first electrode 33 and the second electrode 34. To ensure a uniform flow, the length (l) is preferably at least 5 times larger than the thickness (t), more preferably at least 10 times larger than the thickness (t), and most preferably at least 20 times larger than the thickness (t).

The first plate electrode 33 contacts the channel, seen in a section perpendicular to the flow direction A1, over a first distance which is equal to the width w, and the second plate electrode 34 contacts the channel, seen in a section perpendicular to the axial direction A1, over a second distance which is equal to the width w. Preferably, the width w is at least 5 times larger than the thickness (t), more preferably at least 10 times larger than the thickness (t), and most preferably at least 20 times larger than the thickness (t).

The inlet passage gradually changes shape from the shape of a tube passage 22 at the inlet end 21 to the shape of the measurement channel at the first channel end 31. The inlet portion 20 is shaped as a tube passage 22 at said inlet end 21, and the tube passage 22 gradually changes from a round tube passage to an oval tube passage, to a more or less rectangular passage 23. In the illustrated embodiment, the outlet portion 40 is identical to the inlet portion 20, but is mounted upside down. The outlet passage gradually changes shape from the shape 43 of the measurement channel at the second channel end 32 to the shape of a tube passage 42 at the outlet end 41.

Figure 6:
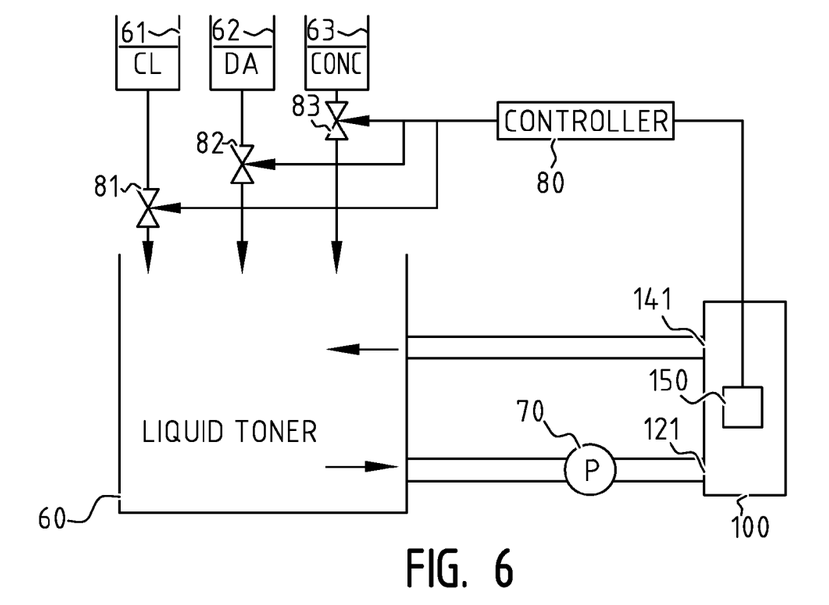
FIG. 6 is a schematic view illustrating the use of a characterization apparatus in a printing apparatus.

FIG. 6 illustrates schematically an exemplary embodiment of a liquid toner storage and conditioning means of a digital printing apparatus using liquid toner. The liquid toner storage and conditioning means comprise a reservoir 60 storing liquid toner for feeding the digital printing apparatus. Further, there is provided a characterization apparatus 100 according to any of the exemplary embodiments disclosed above, and a pump 70 for pumping toner liquid from an inlet end 121 of the characterization apparatus 100 though the measurement channel to an outlet end 141 of the characterization apparatus 100. The liquid toner storage and conditioning means further comprise a reservoir with carrier liquid (CL) 61, a reservoir with dispersing agent (DA) 62, and a reservoir with toner concentrate 63, and a controller 80 configured for controlling valves 81, 82, 83 in function of the values measured by the measurement device 150 of the characterization apparatus 100. The valves 81, 82, 83 are arranged for adding carrier liquid (CL) from reservoir 61, dispersing agent (DA) 62 from reservoir 62, and toner concentrate from reservoir 63, respectively. In that way, these toner components may be added as necessary in function of the measured values or in function of the solid content and the conductivity of the toner liquid, computed based on the measured values.

Figure 7:
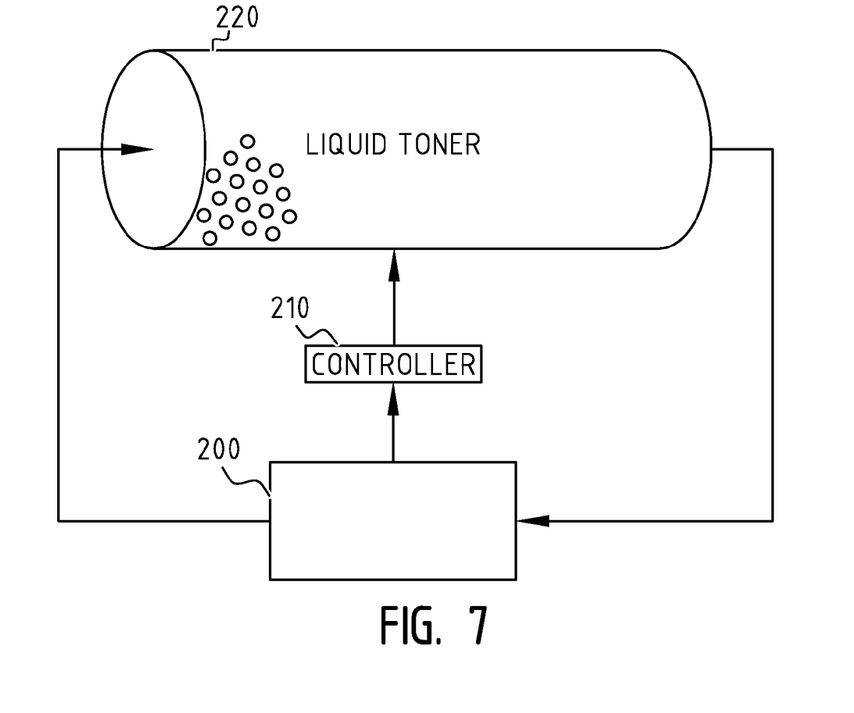
FIG. 7 is a schematic view illustrating the use of a toner preparation apparatus making use of an embodiment of a characterization apparatus.

FIG. 7 illustrates an embodiment of a toner preparation apparatus for preparing liquid toner comprising a characterization apparatus 200 according to any one of the above disclosed embodiments. The toner preparation apparatus comprises a milling means 220 in the form of a substantially horizontally oriented rotating cylinder, and a controller 210 for controlling the milling means 220 in function of the electric measure measured by the measurement device of the characterization apparatus 200. The controller 210 may be configured to stop the milling means 220 when the conductivity of the liquid toner, which is computed based on the measurements, is within a certain range. The toner preparation apparatus may further comprise a dispersion agent adding means (not shown), and the controller 220 may be configured to control the dispersion agent adding means in function of the computed conductivity. In exemplary embodiments the controller 220 may be configured to control a rotation speed of the milling means and/or a cooling module of the milling means in function of the computed conductivity.

Figure 8:
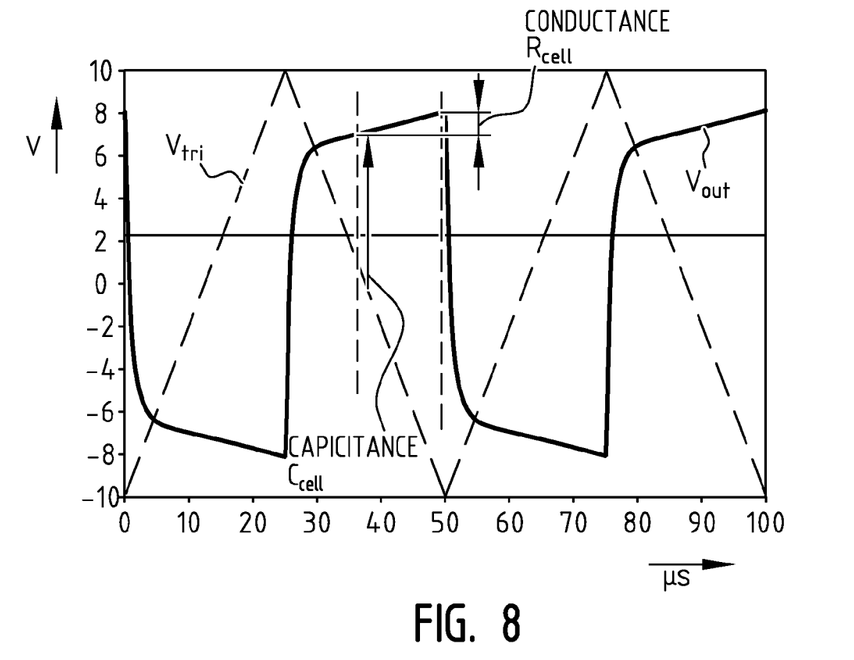
FIG. 8 is a graph showing a periodic wave applied between the first and second electrode and the output voltage generated by applying said periodic wave, in function of the time.

Now an example of a measurement using an embodiment of a characterization apparatus, as well as the deduction of the conductivity and the solid content of liquid toner from the measurements, will be discussed in detail referring to FIGS. 8 and 9. A variable voltage signal, e.g. a triangular signal Vtri of 20 Vpp of sufficient high frequency is applied between the first and the second electrode of the characterization apparatus, see FIG. 8, and a liquid toner is pumped from the inlet passage to the outlet passage, such that liquid toner is present between the first electrode and the second electrode. The first and second electrode form a capacitor submerged in the liquid toner. The dielectric of the capacitor is formed by the liquid toner. The probe 910 formed by the first and second electrode in the liquid toner can be represented as a capacitance Ccell in parallel with a resistance Rcell, see FIG. 9. The measurement device preferably comprises a current amplifier 900 for amplifying the current. In an exemplary embodiment the current amplifier has an output waveform Vout as shown in FIG. 8. The amplitude of the output voltage signal Vout gives a measure for the capacitance Ccell, and the slope of the output voltage signal Vout gives a measure for the conductance Rcell of the toner liquid. To get an accurate measurement and avoid electrophorese, preferably, an AC driving signal Vtri of sufficient high frequency is applied, e.g. between 5 kHz and 50 kHz, depending on the size of the electrodes. The signal of the conductance measurement is typically quite small, and hence a relatively high amplitude of Vtri is preferred, e.g. between −10 V tot 10 V.

The conductivity is derived from the conductance of the electrical signal. A good toner has a very low conductivity to hold its charge during the development stage in the printing process. During manufacturing of the toner, the conductivity may initially have a high value of e.g. 1000 pS/cm and the conductivity may decrease to a value below 1 pS/cm.

The solid content may be derived from the permittivity of the liquid toner, and the permittivity is derived from the capacitance of the probe, i.e. from Ccell.

The measurement signals are sensitive to external influences, and in preferred embodiments the measurement device is shielded from the environment as in the exemplary embodiments of the characterizing apparatus that have been disclosed above.

Since the triangular wave may have some distortion, in preferred embodiments Vtri is also measured and used it in the calculations to improve the stability and resolution of the calculated result for Rcell and Ccell.

The output voltage Vout may be measured e.g. for only part of the period of the triangular signal Vtri. In a possible implementation a number of samples are measured, e.g. a first sample at the zero crossing of the triangular signal Vtri, a second sample when the triangular signal Vtri reaches −10V, and optionally also a number of intermediate samples. These measurements of Vout may then be used to compute the conductivity and/or the solid content of the liquid.

Preferably the measurement device includes a temperature sensor, such as a one-wire digital thermometer. Typically the conductivity is highly temperature dependent, and depending on the required resolution, the temperature may be taken into account.

Now an exemplary embodiment of the method for computing Rcell and Ccell will be explained. In a first step the period of the triangular signal Vtri is measured. In a second step n periods are averaged to get one noise free pattern describing the wave Vtri applied to the cell. This noise free signal is called Vtriangle. In a third step the positive alternation of the cell output Vout is measured.

Figure 9:
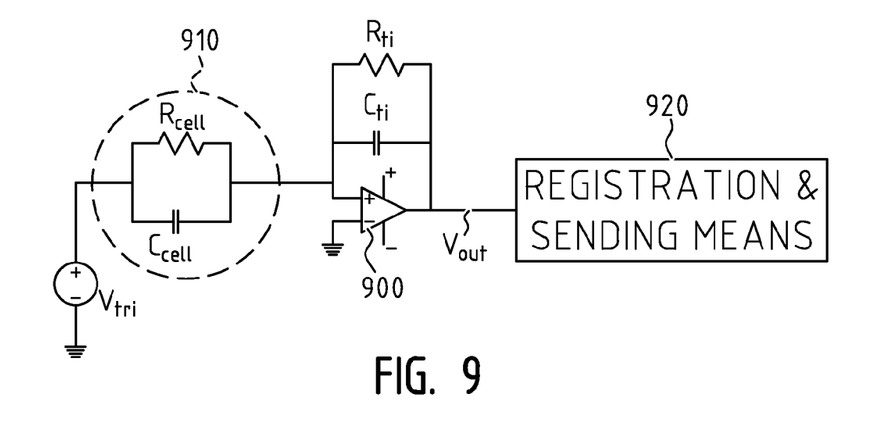
FIG. 9 illustrates schematically an embodiment of a characterizing system of the invention.

The response of the cell can be approximated by an RC-network, see FIG. 9, where Rcell and Ccell are the resistance and capacitance of the cell, i.e. of the capacitor formed by the first and second electrode and the liquid toner located between the first and second electrode; and Rti and Cti are the resistance and capacitance associated with the current amplifier.

Ccell can be reliably estimated, typically within a few %, from the amplitude of Vout at the zero crossing of the slope of the triangular wave Vtri. Rcell can be iteratively calculated by choosing a value for it and applying the transfer curve (TF=Vout/Vtriangle; wherein TF is a function of Rcell, Ccell, Rti, Cti) on the measured samples Vtriangle. Comparing the calculated results with Vout and applying a least means square function (LMS) on it, makes it possible to converge to a value representing the most accurate Rcell:

$$LMS = \Sigma(Vout[z^k] - Vtriangle[z^k]TF[z])^2$$

wherein k is an index referring to a sample number. The initial guess value may be derived from the slope of the output voltage Vout (i.e. assuming that the triangular wave Vtri is perfect).

In further developed embodiments, in order to eliminate offsets in the measurement system and improve the accuracy of the capacitance measurement, the capacitance Ccell may also be determined based on the negative period of the triangular signal Vtri, and the value obtained for the negative period may be averaged with the value obtained for the positive period.

In an exemplary embodiment, the measurement device may comprises an amplifier 900 configured for amplifying the electric current between the first and the second electrode, registration means for registering measures representative for the amplified current, and sending means for sending values derived from or based on the registered measure to an external device. In FIG. 9 the registration and sending means are shown as a single block 920. Further, there may be provided a computing device (not shown) configured for receiving the values derived from or based on the registered measures, and for computing a value for the conductivity and solid content of the liquid containing insoluble particles, based on said received values. More in particular, the computing device may be configured to perform any of the above disclosed algorithms for computing Rcell and Ccell, and for computing the conductivity and solid content of the liquid toner based on Rcell and Ccell.

The skilled person understands that t is also possible to send a known variable current between the electrodes and to measure values representative for the resulting voltage over the electrodes, instead of applying a variable voltage and measuring values representative for the current between the electrodes.

It should be appreciated by those skilled in the art that any block diagrams herein represent conceptual views of illustrative circuitry embodying the principles of the invention. Similarly, it will be appreciated that any flow charts, flow diagrams, state transition diagrams, pseudo code, and the like represent various processes which may be substantially represented in computer readable medium and so executed by a computer or processor, whether or not such computer or processor is explicitly shown.

Whilst the principles of the invention have been set out above in connection with specific embodiments, it is to be understood that this description is merely made by way of example and not as a limitation of the scope of protection which is determined by the appended claims.

The invention claimed is:

1. A characterization apparatus for characterizing a liquid containing insoluble particles; said characterization apparatus comprising:
   a housing comprising an inlet portion defining an inlet passage between an inlet end and a first channel end, a channel portion defining a measurement channel between the first channel end and a second channel end, and an outlet portion defining an outlet passage between the second channel end and an outlet end, such that the liquid can be circulated from said inlet passage, through said measurement channel, to said outlet passage; said channel portion comprising a first electrode and a second electrode at a first and second side of the channel; and
   a measurement device configured for measuring an electric measure representative for properties of the liquid flowing between the first electrode and the second electrode;
   said measurement channel having a length in a flow direction between said first channel end and said second channel end, and a thickness seen in a direction perpendicular to the flow direction corresponding with a distance between said first and said second electrode; said length being at least five times larger than said thickness;
   said inlet passage gradually changing shape from said inlet end to said first channel end; and said outlet passage gradually changing shape from said second channel end to said outlet end.

2. The characterization apparatus of claim 1, wherein said first electrode contacts said channel, in a section perpendicular to the flow direction, over a first distance, and said second electrode contacts said channel, in a section perpendicular to the flow direction, over a second distance; with said first and second distance being at least five times larger than said thickness.

3. The characterization apparatus of claim 1, further comprising a voltage source configured for applying a voltage between the first and the second electrode, wherein the measurement device is configured for measuring values representative for the electric current flowing through the liquid between the first and the second electrode.

4. The characterization apparatus of claim 1, wherein said inlet passage gradually changes shape from the shape of a tube passage at said inlet end to the shape of the measurement channel at said first channel end.

5. The characterization apparatus of claim 1, wherein said outlet passage gradually changes from the shape of the measurement channel at said second channel end to the shape of a tube passage at said outlet end.

6. The characterization apparatus of claim 1, wherein said inlet passage, said measurement channel, and said outlet passage are shaped for creating a flow of said liquid in said measurement channel in the flow direction, such that said flow, seen in a 90% of a section perpendicular to said flow direction, has an average velocity va, and the velocity v in any point of the section fulfills $va-0.1*va<v<va+0.1*va$.

7. The characterization apparatus of claim 1, wherein said first electrode is an inner cylinder and said second electrode is an outer cylinder placed around said inner cylinder, and wherein said outer and inner cylinders define the measurement channel.

8. The characterization apparatus of claim 7, wherein the measurement device is located inside the inner cylinder.

9. The characterization apparatus of claim 1, wherein said first and second electrode are plates spaced at a constant distance from each other.

10. The characterization apparatus of claim 1, wherein the inlet portion is shaped with a tube passage at said inlet end, said tube passage connecting to a ring shaped passage, said ring shaped passage connecting to the first channel end of the measurement channel, said tube passage and said ring shaped passage together forming the inlet passage.

11. The characterization apparatus of claim 10, wherein the tube passage is offset of the measurement channel, and said ring passage gradually narrows as the distance from the tube passage increases.

12. The characterization apparatus of claim 1, wherein the measurement device comprises registration means for registering measures representative for the electric current between the first and the second electrode, and sending means for sending values derived from or based on the registered measures to an external device.

13. The characterization apparatus of claim 1, wherein at least one of the first and the second electrode is provided with a coating.

14. The characterization apparatus of claim 13, wherein the coating is any one of the following: a composite coating including metallic and non-metallic materials, a nickel-PTFE composite coating, a zinc-coating, a nickel plating, a coating obtained by chromatising, a coating obtained by anodizing, a gold plating, a silver plating, a coating obtained by phosphatising, a polytetrafluoroethylene (PTFE)-based coating, a varnish, lacquer coating, a ceramic coating.

15. A characterization system comprising the characterization apparatus of claim 12 and a computing device configured for receiving the values derived from or based on the registered measures, and for computing a value for the conductivity and/or solid content of the liquid containing insoluble particles, based on said received values.

16. A digital printing apparatus using liquid toner comprising:
   a reservoir storing liquid toner; and
   a characterization apparatus for characterizing a liquid containing insoluble particles; said characterization apparatus comprising:
      a housing comprising an inlet portion defining an inlet passage between an inlet end and a first channel end, a channel portion defining a measurement channel between the first channel end and a second channel end, and an outlet portion defining an outlet passage between the second channel end and an outlet end, such that the liquid can be circulated from said inlet passage, through said measurement channel, to said outlet passage; said channel portion comprising a first electrode and a second electrode at a first and second side of the channel;
      a measurement device configured for measuring an electric measure representative for properties of the liquid flowing between the first electrode and the second electrode; said measurement channel having a length in a flow direction between said first channel end and said second channel end, and a thickness seen in a direction perpendicular to the flow direction corresponding with a distance between said first and said second electrode; said length being at least five times larger than said thickness;
      said inlet passage gradually changing shape from said inlet end to said first channel end; and said outlet passage gradually changing shape from said second channel end to said outlet end;

said inlet end of said characterization apparatus being in fluid communication with an outlet of the reservoir.

17. The digital printing apparatus of claim 16, further comprising a toner component addition means for adding a toner component of said liquid toner, and control means configured for controlling said toner component addition means in function of the measurements performed by the measurement device of the characterization apparatus.

18. The digital printing apparatus of claim 16, further comprising a voltage source configured for applying a voltage between the first and the second electrode, wherein the measurement device is configured for measuring values representative for the electric current flowing through the liquid between the first and the second electrode.

19. The digital printing apparatus of claim 16, wherein said inlet passage, said measurement channel, and said outlet passage are shaped for creating a flow of said liquid in said measurement channel in the flow direction, such that said flow, seen in a 90% of a section perpendicular to said flow direction, has an average velocity va, and the velocity v in any point of the section fulfills va−0.1*va<v<va+0.1*va.

20. A toner preparation apparatus for preparing a liquid toner, comprising a characterization apparatus for characterizing a liquid containing insoluble particles; said characterization apparatus comprising:

a housing comprising an inlet portion defining an inlet passage between an inlet end and a first channel end, a channel portion defining a measurement channel between the first channel end and a second channel end, and an outlet portion defining an outlet passage between the second channel end and an outlet end, such that the liquid can be circulated from said inlet passage, through said measurement channel, to said outlet passage; said channel portion comprising a first electrode and a second electrode at a first and second side of the channel; and a measurement device configured for measuring an electric measure representative for properties of the liquid flowing between the first electrode and the second electrode;

said measurement channel having a length in a flow direction between said first channel end and said second channel end, and a thickness seen in a direction perpendicular to the flow direction corresponding with a distance between said first and said second electrode; said length being at least five times larger than said thickness;

said inlet passage gradually changing shape from said inlet end to said first channel end; and said outlet passage gradually changing shape from said second channel end to said outlet end; a milling means; and a controller for controlling the milling means in function of the measurements performed by the measurement device of the characterization apparatus.

* * * * *